United States Patent
Scott et al.

(10) Patent No.: US 6,407,075 B1
(45) Date of Patent: Jun. 18, 2002

(54) FATTY ACID TREATMENT

(76) Inventors: Catherine A. Scott, c/o 33 Hanbury Close, Cheshunt, Waltham Cross, Herts (GB), EN8 9BZ; David F. Horrobin, Laxdale Ltd. Kings Park House, Laurelhill Business Park, Stirling (GB), FK7 9JQ ( * ) Notice: Subject to any disclaimer, the term of this patent is extended or adjusted under 35 U.S.C. 154(b) by 0 days.

(21) Appl. No.: 09/254,286

(22) PCT Filed: Sep. 2, 1997

(86) PCT No.: PCT/GB97/02362

§ 371 (c)(1),
(2), (4) Date: Jul. 6, 1999

(87) PCT Pub. No.: WO98/09621

PCT Pub. Date: Mar. 12, 1998

(30) Foreign Application Priority Data

Sep. 4, 1996 (GB) ............................................. 9618420

(51) Int. Cl.[7] .......................... A61K 31/70; A61K 31/20
(52) U.S. Cl. .......................................... 514/34; 514/560
(58) Field of Search .................................... 514/34, 560

(56) References Cited

FOREIGN PATENT DOCUMENTS

| EP | 0 257 939 | 3/1988 |
|----|-----------|--------|
| GB | 2 114 885 | 9/1983 |

OTHER PUBLICATIONS

Carter et al., Chemotherapy of Cancer, second edition, John Wiley & Sons N.Y., N.Y.,PP90–93, Aug. 13, 1981.*

Database WPI Week 8849 Derwent Publications Ltd., London, GB; AN 88–348779 XP002054538 & JP 63 258 816 A (Nippon Oils & Fats Co. Ltd.), Apr. 16, 1987 see abstract.

Ferguson PJ: "Cytotoxic and chemomodulative effects of gamma–linolenic acid (GLA) against a human squamous carcinoma line and multidrug–resistant (MDR) and carboplatin–resistant (CP–R) variants (Meeting abstract)." Proc Annu Meet AM Assoc Cancer Res;36:A1722 1995, XP002054537 see abstract.

* cited by examiner

Primary Examiner—Jerome D. Goldberg

(57) ABSTRACT

The use in preparation of a medicament for treating and preventing the side effects of anti-cancer chemotherapy of a polyunsaturated fatty acid with a carbon chain length of 14 to 26 and with 2 to 6 double bonds in the molecule in cis or trans configuration, and a method of such treatment or prevention wherein said fatty acid is used as an active.

2 Claims, No Drawings

FATTY ACID TREATMENT

FIELD OF THE INVENTION

The invention relates to fatty acid treatment.

BACKGROUND

Chemotherapy, the use of drugs which aim either to kill cancer cells or to stop the spread of cancer, is now one of the most widely used types of treatment for cancer. It may be used either alone or in combination with one of the other modalities of cancer treatment, usually surgery or radiotherapy. Most chemotherapy regimes, other than those primarily targeted at the endocrine system such as anti-oestrogens and antiandrogens, cause important side effects. These side effects differ from drug to drug, but it is now common to use two, three, four or more drugs in combination in chemotherapy regimes and so most chemotherapy-treated patients will experience one or more of the typical consequences. The side effects include nausea, vomiting, suppression of the immune system, suppression of white blood cells and platelets, hair loss, cardiovascular damage, lung damage, renal damage, nerve damage and marked fatigue and malaise. Each drug has a specific range of side effects, some of which may be particularly important and limit the dose of the drug which can be given and so reduce the likelihood of a cure. Doxorubicin and related compounds, for example, can be severely cardiotoxic and this is a common dose-limiting side effect. Bleomycin, and to a lesser extent cyclophosphamide, can be toxic to the lungs causing fibrosis. The platinum derivatives and related compounds may be very toxic to the nerves.

We have been developing gamma-linolenic acid (GLA) and related compounds, including linoleic acid (LA), dihomogammalinolenic acid (DGLA), arachidonic acid (AA), stearidonic acid (SA), alpha-linolenic acid (ALA), eicosapentaenoic acid (EPA) and docosahexaenoic acid (DHA) for the treatment of cancer. These compounds which are all polyunsaturated lipids are cytotoxic to many cancer cells at concentrations which do not harm normal cells and also have a range of anti-metastatic effects which may be operative at lower concentrations. We have come to the conclusion that many unsaturated fatty acids with carbon chain lengths from 14 to 26 and which contain two to six unsaturated double carbon-carbon bonds which may be either in the cis or the trans configuration can have anti-cancer actions. Other examples of such fatty acids include conjugated linoleic acid and parinaric acid, but the natural n-6 and n-3 EFAS are set out in the following:

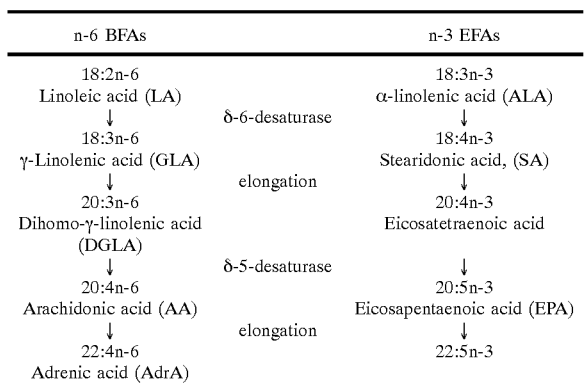

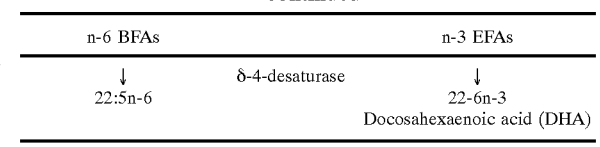

The acids, which in nature are of the all—cis configuration, are systematically named as derivatives of the corresponding octadecanoic, eicosanoic or docosanoic acids, e.g. LA z,z-octadeca—9,12 —dienoic acid or DHA z,z,z,z,z,z—docosa—4,7,10,13,16,19 —hexanoic acid, but numerical designations based on the number of carbon atoms, the number of centres of unsaturation and the number of carbon atoms from the end of the chain to where the unsaturation begins, such as correspondingly, 18:2 n-6 or 22:6 n-3, are convenient. Initials, e.g. EPA, and shortened forms of the name e.g. eicosapentaenoic acid, are used as trivial names in some instances.

CURRENT WORK

In a range of studies we have administered GLA, LA, EPA and DHA to patients with cancer and we are actively developing specific derivatives of these fatty acids as anti-cancer drugs. In many instances, the fatty acids have been given to patients who at that same time were receiving conventional chemotherapy for their cancer. We have repeatedly observed that many of the toxic side effects of chemotherapy are substantially reduced in patients who at the same time are receiving one or more of LA, GLA, EPA and DHA. On theoretical grounds, because of their similar chemical characteristics and modes of action we believe that many of the other fatty acids whose general characteristics are summarised in the previous paragraph will also have similar effects. The effects observed include reduced hair loss, reduced suppression of leukocytes and lymphocytes, reduced nausea and vomiting and in particular reduced fatigue and malaise. Our observations therefore indicate that GLA and EPA and related compounds may surprisingly have a broad spectrum of actions in reducing many different side effects of chemotherapy. We therefore propose their use in patients who are receiving chemotherapy for cancer to reduce the side effects of such chemotherapy, as set out in the claims herein.

We have recently supported the clinical observations by animal studies on the cardiotoxicity of doxorubicin and the lung toxicity of bleomycin. When 20 mg of doxorubicin (DOX) is given intraperitoneally to mice, the animals usually die within two weeks because of cardiac damage. When animals were pre-treated with LA or with GLA or with EPA or with DHA in various doses and chemical forms, the death rate to the same dose of doxorubicin was reduced to between 20% and 60% depending on the dose and the precise chemical administered. In addition the reduction in cardiac weight, which is characteristic of doxorubicin toxicity, was considerably attenuated. Similarly, bleomycin introduced into the trachea of animals under anaesthesia at a dose of about 5–10 IU per kg body weight, within 2–4 weeks the animals develop severe lung fibrosis which is very similar to the fibrosis which occurs in human patients treated with bleomycin. Treatment with gamma-linolenic acid and linoleic acid could almost entirely suppress the lung pathological changes and the increased production of fibrous tissue. In a third animal study, the anti-cancer streptozotocin was used. A major effect of this compound is to damage the islet cells of the pancreas and consequently to lead to insulin dependent diabetes. Administration of LA, GLA or EPA prior to the streptozotocin greatly reduced the likelihood of the development of diabetes in rats. The ability of the fatty acids to suppress these very different forms of toxicity and the clinical observations which have been made in patients being treated with a wide range of drugs suggest that this is a method of preventing drug toxicity which has wide applicability.

THE INVENTION

The invention is as set out in the claims, but broadly lies in the use, in preparation of a medicament for treating and preventing the side effects of anti-cancer chemotherapy, particularly the side effects caused by any of the drugs listed herein, of a polyunsaturated fatty acid with a carbon chain length of 14 to 26 and with 2 to 6 double bonds in the molecule in cis or trans configuration, and a method of such treatment or prevention wherein said fatty acid is administered.

Preferred fatty acids are LA, GLA, DGLA, SA, ALA, EPA and DHA, optionally administered or used with other fatty acids.

The drugs which have been used in anti-cancer chemotherapy in patients as referred to above include methotrexate, 5-fluorouracil, cyclophosphamide, cisplatin, doxorubicin, taxol and vincristine, but the invention provides a method of reducing the side effects resulting from any form of cancer chemotherapy resulting from drugs in any one of the classes mentioned below, or drugs similar to them which may be developed in the future:

Folate antagonists such as methotrexate and trimetrexate

Pyrimidine antagonists such as 5-fluorouracil, fluorodeoxyuridine and azacytidine.

Purine antagonists such as mercaptopurine, thioguanine, tiazofurin, chloro-deoxyadenosine and pentostatin.

Sugar modified analogues such as cytarabine and fludarabine.

Ribonucleotide reductase inhibitors such as hydroxyurea.

Nitrogen mustards such as mechlorethamine, chlorambucil, melphalan cyclophosphamide and ifosfamide.

Aziridines such as thiotepa, altretamine and mitomycin.

Alkane sulfonates such as busulfan.

Nitrosoureas such as carmustine, lomustine, semustine and streptozotocin.

Platinum compounds such as cisplatin and carboplatin.

Methylating agents such as dacarbazine and procarbazine.

DNA-binding drugs such as daunorubicin, doxorubicin, idarubicin, epirubicin, mitoxantrone, dactinomycin, bleomycin and plicamycin.

Topoisomerase inhibitors such as etoposide, teniposide, amascrine, camptothecin.

Microtubule active agents such as vinblastine, vincristine, vindosine, taxol and taxotere.

The fatty acids may be administered at the same time as the anti-cancer drugs or preferably both prior to and during therapy with the anti-cancer drugs themselves administered in amounts appropriate for the individual drug. The doses of the fatty acids may be from 1 mg to 100 g per day, preferably 50 mg to 50 g per day and very preferably 500 mg to 20 g per day. The fatty acids may be given in any appropriate form which leads to an elevation of the fatty acid in the blood and cell membranes, including free fatty acids, simple esters of various sorts, salts including lithium salts, mono-, di- and tri-glycerides, mono- and di-esters of dihydric alcohols, ascorbyl and niacin derivatives, cholesterol esters, phospholipids and any other appropriate carriers. They may be given orally, parenterally or topically using any appropriate carrier or delivery systems or excipients known to those skilled in the art, including capsules, tablets, powders, liquids, emulsions and any other appropriate method.

FORMULATION EXAMPLES

The chemotherapy drugs can be administered in the manner conventional for each drug, itself known and no part of the invention. The fatty acids may be in any convenient form and the following are examples, suited also to the other fatty acids discussed.

1. Administration of 500 mg to 20 g of GLA per day in the form of soft or hard gelatine capsules or tablets providing:
   a. 40 to 80 mg per capsule of GLA in the form of evening primrose oil.
   b. 50–150 mg per capsule of GLA in the form of borage, blackcurrant, fungal or other appropriate oil.
   c. 100–500 mg GLA per capsule in the form of triglyceride GLA, or any appropriate salt of GLA, such as the lithium or calcium or magnesium or zinc or potassium salts.
2. Administration of DGLA in a dose of 500 mg to 20 g per day in the forms of 1c above.
3. Administration of GLA or DGLA in association with EPA, with or without DHA. for example as a 40 to 80 mg GLA per capsule in the form of evening primrose oil together with 10 mg to 100 mg per capsule of EPA in the form of cold water marine fish oil.
4. Administration of GLA or DGLA in the form of a soluble powder or effervescent granule formed from any appropriate salt of GLA as in 1c above and excipients such as citric acid monohydrate, sodium bicarbonate or other dibasic acids such as tartaric or maleic acid plus sweeteners such as sucrose or sorbitol and flavourings.
5. Administration of GLA or DGLA in the form of liquid evening primrose, borage or other appropriate oil as the oil itself or as a whip or emulsion prepared with appropriate flavours and stabilisers known to those skilled in the art.,
6. Administration of GLA or DGLA in any appropriate chemical form, microencapsulated using starch, gelatine, gum arabic or other appropriate formulation known to those skilled in the art.,
7. Administration of GLA in the form of pessaries, suppositories, skin patches or any other appropriate route.
8. A parenteral lipid emulsion is used containing 10% total lipid by volume in a per se conventional pyrogen-free formulation "INTRALIPID" oil in water emulsion (trade mark, Kabi-Vitrum) containing per 500 ml water at pH7:

| | |
|---|---|
| Fractionated Soybean oil | 50 g |
| Fractionated egg phospholipids | 6 g |
| Glycerol | 11 g |

According to the invention (a) 5%, (b) 10% or (c) 15% of the lipid present, by weight, is taken up by one or other of the mixtures of EFAs below, the EFAs being provided as triglycerides, or free fatty acids, or ethyl esters, or diol esters as in our PCT specifications WO 96/34846 (PCT GB 96/01053) and WO 96/34855 (PCT GB 96 01052), or appropriate salts, including the lithium salts. The following figures show the proportional composition of the added EFA or EFA mixture:

| GLA | DGLA | SA | EPA | DHA |
|-----|------|-----|-----|-----|
| 100 | — | — | — | — |
| 50 | 50 | — | — | — |
| 50 | — | 50 | — | — |
| 50 | — | — | 30 | 20 |
| — | 60 | — | 20 | 20 |
| — | 80 | 20 | — | — |
| 80 | — | — | 20 | 10 |
| — | — | — | 80 | 20 |

An oil-in-water oral emulsion (batch size 200 g) was prepared containing the following ingredients, the galactolipid being as described in PCT specification WO 95/20943 (PCT SE 95/00115):

| Ingredients | % wt. |
|-------------|-------|
| Emulsifier (galactolipid)* | 2.00 |
| 1,3-Propane diol diester (GLA-EPA) (as in Example 8) | 20.00 |
| Ascorbyl palmitate (AP) | 0.02 |
| Vitamin E | 0.5 |
| Water | to 100.00 |

The emulsifier-galactolipid was distersed in the diester, and the Vitamin E, AP and water were mixed. The oil phase was added to the aqueous phase under a high shear mix (Ultraturrax—trade mark) at speed 4, for a few minutes. This pre-emulsion was then homogenised at 80 MPA and at 50° C. for 6 cycles (mini-Lab 8.30 H; APV Rannie AS, Denmark). The emulsion formed had an average droplet size of 230 nm.

CASE HISTORIES

The following histories illustrate use of the invention

A. A patient with malignant brain cancer, a glioblastoma, was treated in addition to surgery with the nitrosourea, carmustine. Prior to and during the carmustine course the patient was also receiving gamma-linolenic acid and linoleic acid in the form of the triglyceride dilinoleoyl-monogammalinolenoyl-glycerol (DLMG). Carmustine normally causes marked nausea and vomiting, anorexia and severe malaise. in contrast, this patient experienced only very mild nausea and felt well throughout indicating reduction of the side effects by the DLMG.

B. A patient with Hodgkin's disease was treated with the 'MOPP' regime (carmustine, vincristine, procarbazine and prednisone). For one week prior to the start of the chemotherapy regime, and throughout the course of chemotherapy, this 40 year old man also received 3 g per day orally of the lithium salt of gammalinolenic acid. This chemotherapy regime normally causes severe vomiting and nausea, marked malaise and anorexia. In contrast, this patient experienced only mild nausea and remained well and able to continue working.

C. A 50 year old woman with breast cancer was treated with the 'CMF' regime (cyclophosphamide, methotrexate and 5-fluorouracil). This regime was started one week after receiving a cumulative dose of 30 g of gammalinolenic acid intravenously as the lithium salt with continued treatment with 2 g/day of oral lithium gamrnalinolenate. The chemotherapy regime normally causes nausea, vomiting, mucositis and white cell suppression. In contrast, this woman experienced only mild nausea with no vomiting or mucositis and the suppression of the white cell count was less than expected.

D. A 55 year old man with metastatic colon cancer was treated with 5-fluorouracil. This normally causes nausea, vomiting, white cell suppression and mucositis. For two weeks prior to the chemotherapy and during the whole of the chemotherapy course, the man also received 3 g/day of the pure triglyceride of eicosapentaenoic acid. There was no vomiting or mucositis and the nausea and white cell suppression were less than expected.

What is claimed is:

1. A method of preventing or treating the side effects of anti-cancer chemotherapy selected from nausea, vomiting, suppression of the immune system, suppression of white blood cells and platelets, hair loss, cardiovascular damage, lung damage, renal damage, nerve damage or marked fatigue and malaise, the method comprising administering to a subject in need thereof an enhanced effective amount of gamma-linolenic acid and an effective amount of doxorubicin.

2. A method of preventing or treating nausea or fatigue as side effects of anti-cancer chemotherapy comprising administering to a subject in need thereof an enhanced effective amount of gamma-linolenic acid and an effective amount of doxorubicin.

* * * * *